(12) United States Patent
Locke et al.

(10) Patent No.: US 11,229,733 B2
(45) Date of Patent: *Jan. 25, 2022

(54) REDUCED-PRESSURE TREATMENT SYSTEMS AND METHODS EMPLOYING A FLUIDLY ISOLATED PUMP CONTROL UNIT

(71) Applicant: KCI Licensing, Inc., San Antonio, TX (US)

(72) Inventors: Christopher Brian Locke, Bournemouth (GB); Aidan Marcus Tout, Alderbury (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 226 days.

This patent is subject to a terminal disclaimer.

(21) Appl. No.: 16/550,579

(22) Filed: Aug. 26, 2019

(65) Prior Publication Data

US 2020/0030500 A1 Jan. 30, 2020

Related U.S. Application Data

(63) Continuation of application No. 13/796,385, filed on Mar. 12, 2013, now Pat. No. 10,434,226, which is a
(Continued)

(51) Int. Cl.
*A61M 27/00* (2006.01)
*A61M 1/00* (2006.01)
(Continued)

(52) U.S. Cl.
CPC ............... *A61M 1/74* (2021.05); *A61M 1/80* (2021.05); *A61M 1/82* (2021.05); *A61M 1/90* (2021.05);
(Continued)

(58) Field of Classification Search
CPC ...... A61M 27/00; A61M 39/00; A61M 39/04; A61M 39/22; A61M 39/26; A61M 39/28;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Tatyana Zalukaeva
*Assistant Examiner* — Ilya Y Treyger

(57) ABSTRACT

Systems, devices, and methods for treating a tissue site on a patient with reduced pressure are presented. In one instance, a reduced-pressure treatment device to treat a tissue site with reduced pressure may include a pump control unit fluidly separate from a collection unit. Pump energy may be provided by the pump control unit to deflect one or more diaphragms within the collection unit to create reduced pressure. Other systems, devices, and methods are presented.

20 Claims, 7 Drawing Sheets

Related U.S. Application Data continuation of application No. 13/108,433, filed on May 16, 2011, now Pat. No. 8,409,160.

(60) Provisional application No. 61/414,738, filed on Nov. 17, 2010, provisional application No. 61/359,205, filed on Jun. 28, 2010, provisional application No. 61/345,821, filed on May 18, 2010, provisional application No. 61/345,830, filed on May 18, 2010.

(51) Int. Cl.
| | |
|---|---|
| A61M 39/00 | (2006.01) |
| A61M 39/04 | (2006.01) |
| A61M 39/22 | (2006.01) |
| A61M 39/26 | (2006.01) |
| A61M 39/28 | (2006.01) |
| F04B 45/00 | (2006.01) |

(52) U.S. Cl.
CPC ....... *A61M 1/0023* (2013.01); *A61M 2205/11* (2013.01); *Y10T 137/3109* (2015.04)

(58) Field of Classification Search
CPC ... A61M 1/0023; A61M 2205/11; F04B 45/00
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,393,187 B2 * | 7/2008 | Weigl ............... F01N 3/2066 417/413.1 |
| 7,503,910 B2 * | 3/2009 | Adahan ............... F04B 43/04 604/319 |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0098097 A1 * | 7/2002 | Singh ............... B01L 3/5027 417/413.1 |
| 2002/0115951 A1 | 8/2002 | Norstrem et al. |
| 2002/0120185 A1 | 8/2002 | Johnson |
| 2002/0143286 A1 | 10/2002 | Tumey |

(56) References Cited

U.S. PATENT DOCUMENTS

| | | | |
|---|---|---|---|
| 2004/0006319 A1* | 1/2004 | Lina | A61M 1/90 604/304 |
| 2007/0213651 A1* | 9/2007 | Busby | A61M 1/281 604/5.04 |
| 2009/0036873 A1* | 2/2009 | Nielsen | A61M 1/80 604/543 |
| 2009/0069761 A1* | 3/2009 | Vogel | A61F 13/0226 604/313 |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" ; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

REDUCED-PRESSURE TREATMENT SYSTEMS AND METHODS EMPLOYING A FLUIDLY ISOLATED PUMP CONTROL UNIT

RELATED APPLICATIONS

This application is a continuation of U.S. patent application Ser. No. 13/796,385, filed Mar. 12, 2013, which is a continuation of U.S. patent application Ser. No. 13/108,433, filed May 16, 2011, now U.S. Pat. No. 8,409,160, which claims the benefit, under 35 USC § 119(e), of the filing of U.S. Provisional Patent Application No. 61/345,821, entitled "Reduced-Pressure Treatment Systems and Methods Employing A Fluidly Isolated Pump Control Unit," filed May 18, 2010, U.S. Provisional Patent Application No. 61/359,205, entitled "Evaporative Body Fluid Containers and Methods," filed Jun. 28, 2010, U.S. Provisional Patent Application No. 61/345,830, entitled "Systems and Methods for Measuring Reduced Pressure Employing An Isolated Fluid Path," filed May 18, 2010, and U.S. Provisional Patent Application No. 61/414,738, entitled "Reduced-Pressure Canisters and Methods for Recycling," filed Nov. 17, 2010. All of the listed applications are incorporated herein by reference for all purposes.

BACKGROUND

The present disclosure relates generally to reduced-pressure medical treatment systems and, more particularly, but not by way of limitation, to reduced-pressure systems and methods employing a fluidly isolated pump control unit.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

SUMMARY

According to an illustrative, non-limiting embodiment, a reduced-pressure treatment device for use with a system for treating a tissue site on a patient with reduced pressure includes a canister unit having a pump head with at least one diaphragm, wherein the pump head is fluidly coupled to the tissue site to provide reduced pressure to the tissue site, and a fluid reservoir fluidly coupled to the pump head for collecting fluid from the tissue site. The reduced-pressure treatment device also includes a pump control unit fluidly separate from the canister unit and operable to provide pump energy to the pump head to cause the pump head to generate reduced pressure. The pump control unit may have a control device and a power system for providing power to the control device. The reduced-pressure treatment device further includes at least one linking interface associated with the canister unit and the pump control unit. The linking interface provides the pump energy to the pump head to generate reduced pressure.

According to another illustrative, non-limiting embodiment, a reduced-pressure treatment system for providing reduced-pressure treatment to a tissue site on a patient includes a manifold for disposing proximate the tissue site, a sealing member for placing over the tissue site and the manifold and operable to form a fluid seal, and a reduced-pressure treatment device. The reduced-pressure treatment device includes a canister unit having a pump head with at least one diaphragm, wherein the pump head is for fluidly coupling to the tissue site to provide reduced pressure to the tissue site, and a fluid reservoir fluidly coupled to the pump head for collecting fluid from the tissue site. The reduced-pressure treatment device also includes a pump control unit that is fluidly separate from the canister unit and operable to provide the pump energy to the pump head to cause the pump head to generate reduced pressure. The pump control unit may have a control device and a power system for providing power to the control device. The reduced-pressure treatment device further includes at least one linking interface associated with the canister unit and the pump control unit. The linking interface provides energy to the pump head to generate reduced pressure.

According to another illustrative, non-limiting embodiment a method of providing reduced-pressure treatment to a tissue site on a patient includes the steps of: placing a manifold proximate the tissue site, disposing a sealing member over the manifold and a patient's epidermis, forming a fluid seal between the sealing member and the patient's epidermis, and delivering reduced pressure to the manifold. The step of delivering reduced pressure to the manifold includes providing an electrical current to a first electromagnet that is substantially aligned with a diaphragm. The first electromagnet is fluidly isolated from the diaphragm. The first electromagnet deflects the diaphragm from a first position to a second position, and the movement of the diaphragm between the first position and the second position causes fluid movement to generate reduced pressure.

Other objects and advantages of the illustrative embodiments will become apparent with reference to the drawings and detailed description that follow.

DETAILED DESCRIPTION OF ILLUSTRATIVE EMBODIMENTS

Figure 1:
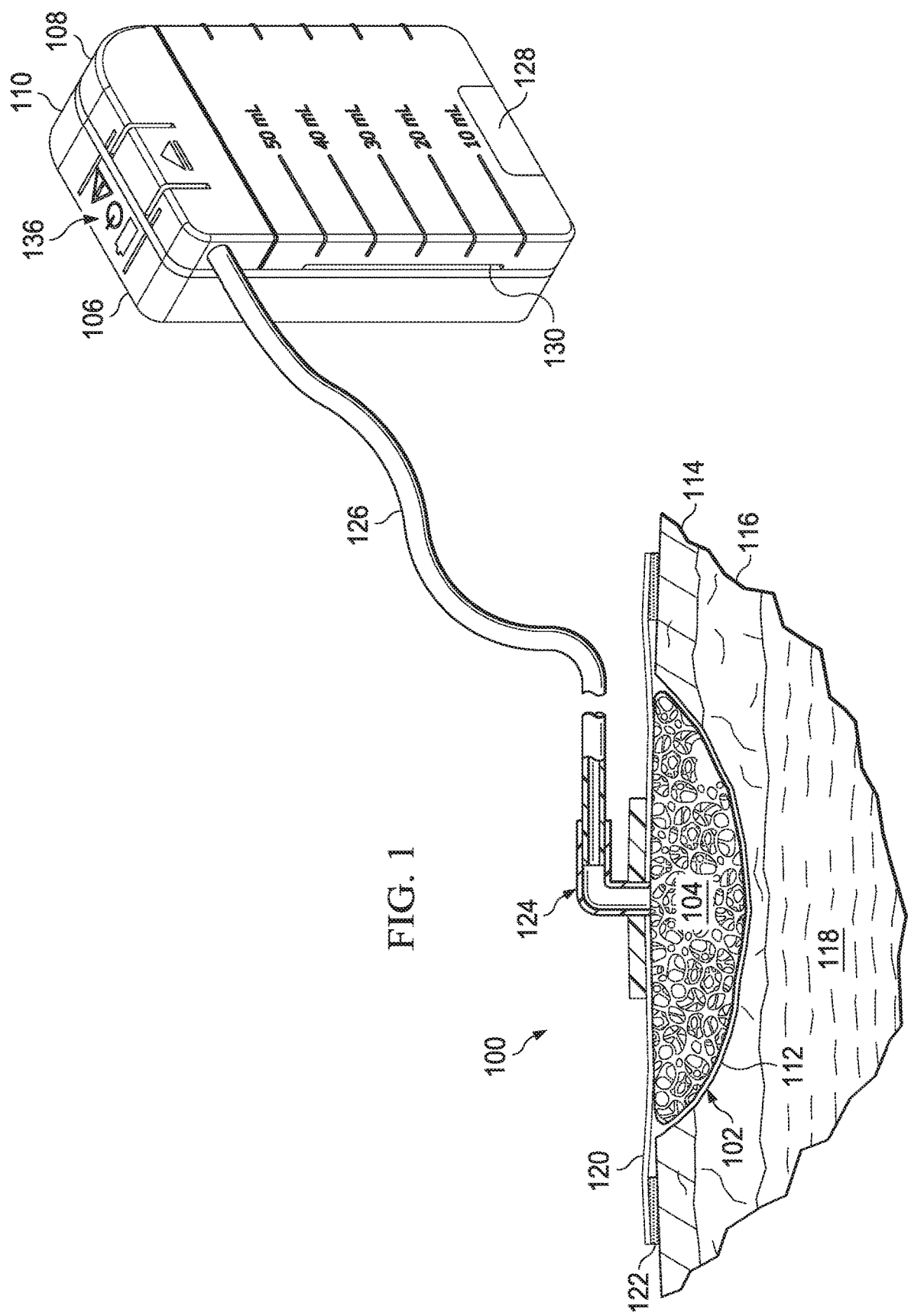
FIG. 1 is a schematic diagram, with a portion shown in cross section and a portion shown in perspective, of an illustrative, non-limiting embodiment of a reduced-pressure treatment system.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Referring to the drawings and primarily to FIGS. 1-5, an illustrative, non-limiting embodiment of a reduced-pressure treatment system 100 for providing reduced-pressure treatment to a tissue site 102 of a patient is presented. The reduced-pressure treatment system 100 includes a manifold 104 placed proximate to the tissue site 102, and a reduced-pressure treatment device 106 that is fluidly coupled to the manifold 104. The reduced-pressure treatment device 106 has a canister unit 108 and a pump control unit 110. The pump control unit 110 is fluidly separate or isolated from the canister unit 108.

Fluidly separating the pump control unit 110 and the canister unit 108 helps prevent the pump control unit 110 from being contaminated by fluids. Separating the pump control unit 110 and the canister unit 108 also facilitates reusing high-value components of the pump control unit 110. Moreover, the separation may, in some embodiments, facilitate making the canister unit 108 disposable. The pump control unit 110 and the canister unit 108 are further described below.

The reduced-pressure treatment system 100 is used to treat the tissue site 102, which may be a wound 112. In one illustrative, non-limiting embodiment, the wound 112 is through or involves epidermis 114, dermis 116, and subcutaneous tissue 118. The reduced-pressure treatment system 100 may also be used at other tissue sites. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

The manifold 104 is disposed proximate to the tissue site 102. In one illustrative embodiment, the manifold 104 is made from a porous and permeable foam or foam-like material and, more particularly, a reticulated, open-cell polyurethane or polyether foam that allows good permeability of wound fluids while under reduced pressure. One such foam material that has been used is the VAC® GranuFoam® Dressing available from Kinetic Concepts, Inc. (KCI) of San Antonio, Tex. Any material or combination of materials may be used for the manifold material provided that the manifold material is operable to distribute the reduced pressure. The manifold is a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

A sealing member 120 is placed over the manifold 104 and a portion of the patient's epidermis 114. The sealing member 120 may be an elastomeric material or any material or substance that provides a fluid seal. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, the sealing member 120 may include a silicone drape, 3M Tegaderm® drape, acrylic drape such as one available from Avery Dennison.

The sealing member 120 may have an attachment device 122 that helps form a fluid seal between the sealing member 120 and the patient's epidermis 114. The attachment device 122 may be used to hold the sealing member 120 against the patient's epidermis 114 or another layer, such as a gasket or additional sealing member. The attachment device 122 may take numerous forms. For example, the attachment device 122 may be a medically acceptable, pressure-sensitive adhesive or a hydrocolloid that extends about a periphery of the sealing member 120. The fluid seal is a seal adequate to maintain reduced pressure at a desired site given the particular reduced-pressure source or subsystem involved.

A reduced-pressure interface 124 may be coupled to the sealing member 120 to provide fluid access to the manifold 104. A reduced-pressure delivery conduit 126 fluidly couples the reduced-pressure treatment device 106 and the reduced-pressure interface 124. In one illustrative embodiment, the reduced-pressure interface 124 is a T.R.A.C.® Pad or Sensa T.R.A.C.® Pad available from KCI of San Antonio, Tex. The reduced-pressure interface 124 allows the reduced pressure to be delivered to the tissue site 102. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 104, the reduced-pressure delivery conduit 126, and proximate the tissue site 102. As the hydrostatic pressure around the tissue site 102 approaches the desired reduced pressure, the flow may subside, and the reduced pressure may be maintained.

Unless otherwise indicated, values of pressure stated herein are gauge pressures. The reduced pressure delivered may be constant or varied (patterned or random) and may be delivered continuously or intermittently. Although the term "negative pressure" may be used to describe the pressure applied to the tissue site, the actual pressure applied to the tissue site 102 may be more than the pressure normally associated with a complete vacuum. Consistent with the use herein, an increase in reduced pressure or vacuum pressure refers to a relative reduction in absolute pressure.

The reduced-pressure treatment device 106 delivers reduced pressure and receives fluids, such as exudates, from the tissue site 102. The reduced-pressure treatment device 106 includes an attaching device, such as clip member 128, to hold the canister unit 108 proximate to the pump control unit 110. The attaching device or clip member 128 in the embodiment shown may hold the canister unit 108 substantially flush against the pump control unit 110. An air gap channel 130 may be formed between the canister unit 108 and the pump control unit 110. A front portion 132 of the canister unit 108 may be transparent to allow fluid within the canister unit 108 to be viewed from outside of the canister unit 108. A graduated scale 134 may be included on the front portion 132 to visually determine the amount of liquids in the canister unit 108. The reduced-pressure delivery conduit 126 fluidly couples to the canister unit 108 to deliver reduced pressure to the tissue site 102 and to deliver fluids from the tissue site 102 to the canister unit 108.

Figure 2:
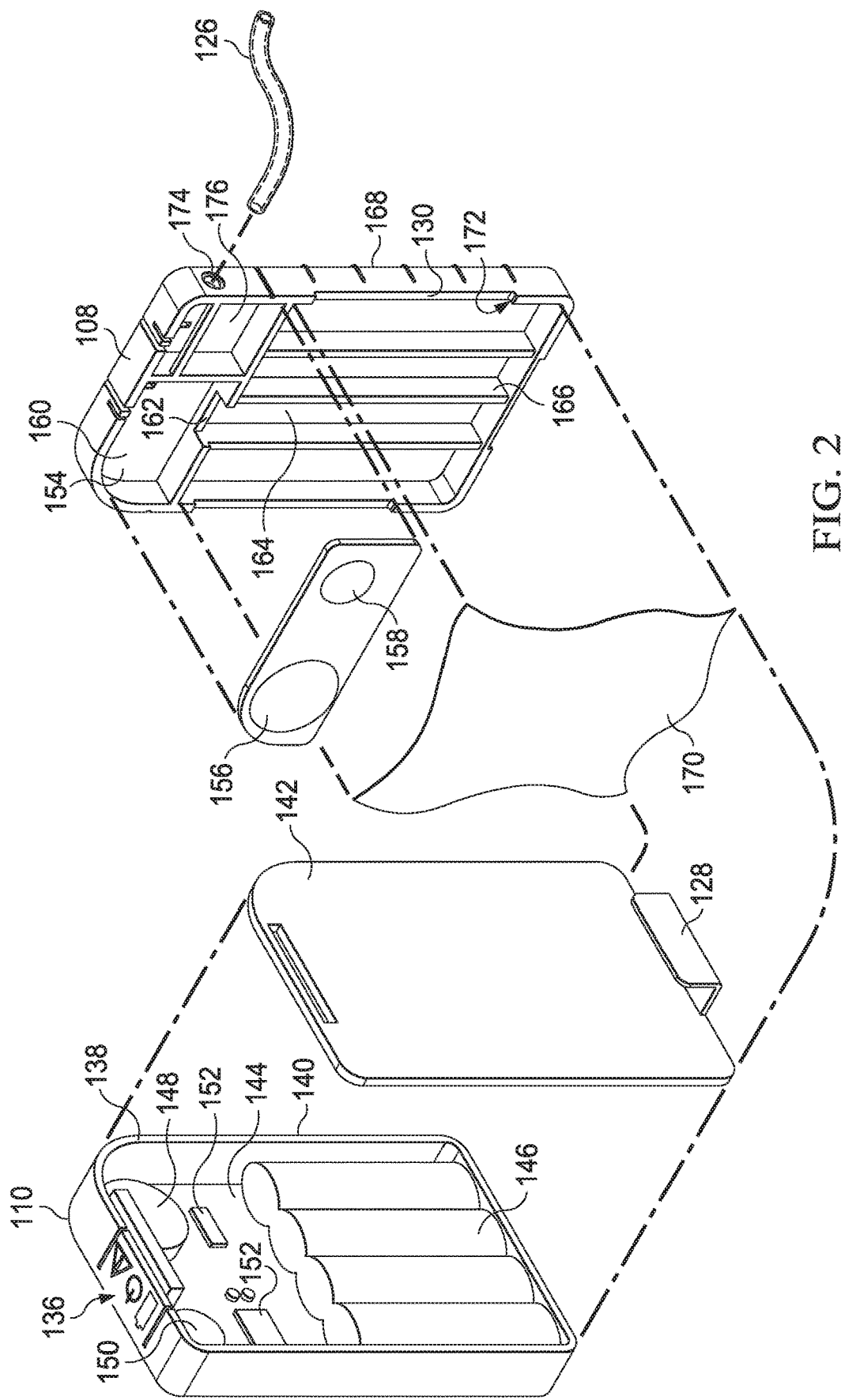
FIG. 2 is a schematic, exploded, perspective view of an illustrative, non-limiting embodiment of a reduced-pressure treatment device.

Referring now primarily to FIG. 2, an exploded view of the reduced-pressure treatment device 106 is presented. The pump control unit 110 may include a pump control unit housing 138 that may include a base portion 140 and a first cover 142. An interior 144 of the base portion 140 may include batteries 146 or other power supply. In one embodiment, the batteries 146 may be recharged by placing the reduced-pressure treatment device 106 on a charging cradle (not shown). The interior 144 may also include a first electromagnet 148 and a second electromagnet 150. The electromagnets 148, 150 may be, for example, electromagnetic coils or solenoids. A control device 152 is included within the interior 144 and provides controlling elements for the electromagnets 148, 150. The control device 152 may also execute inputs from a user interface device 136 as described below. The cover 142 is sized and configured to mate with the base portion 140 and provide a substantially fluid tight seal therewith. The cover 142 may be removably or permanently joined to the base portion 140 by welding, fasteners, or other coupling techniques.

The pump control unit 110 is configured to be held in close proximity to the canister unit 108. In the illustrative embodiment, the canister unit 108 is made to be placed inside of the clip member 128 and form an interference fit to hold the canister unit 108 against the pump control unit 110. It should be understood that numerous other techniques and devices may be used for holding the pump control unit 110 in close proximity to the canister unit 108.

The canister unit 108 includes a pump head 154. The pump head 154 may include one or more diaphragms, such as a first diaphragm 156 and a second diaphragm 158. The diaphragm includes a sheet of semi-flexible or flexible material anchored at the sheet's periphery to a wall. The pump head 154 may further include a pump chamber 160. The pump head 154 is operable to produce a reduced pressure that is delivered through a conduit or aperture 162 to a fluid reservoir 164, which may include one or more baffles 166. The canister unit 108 has a base portion 168 and a membrane 170. The membrane 170 may be vapor permeable. The membrane 170 covers at least a portion of the fluid reservoir 164 and may be supported in part by the baffles 166. The base portion 168 of the canister unit 108 includes a recessed portion 172 that forms the air gap channel 130 between the canister unit 108 and the pump control unit 110 when assembled. The membrane 170 may be an ultra high moisture-vapor transmission ratio (MVTR) membrane that allows water vapor to pass from the fluid reservoir 164 to atmosphere. The air gap channel 130 facilitates the transfer of the water vapor.

Figure 3:
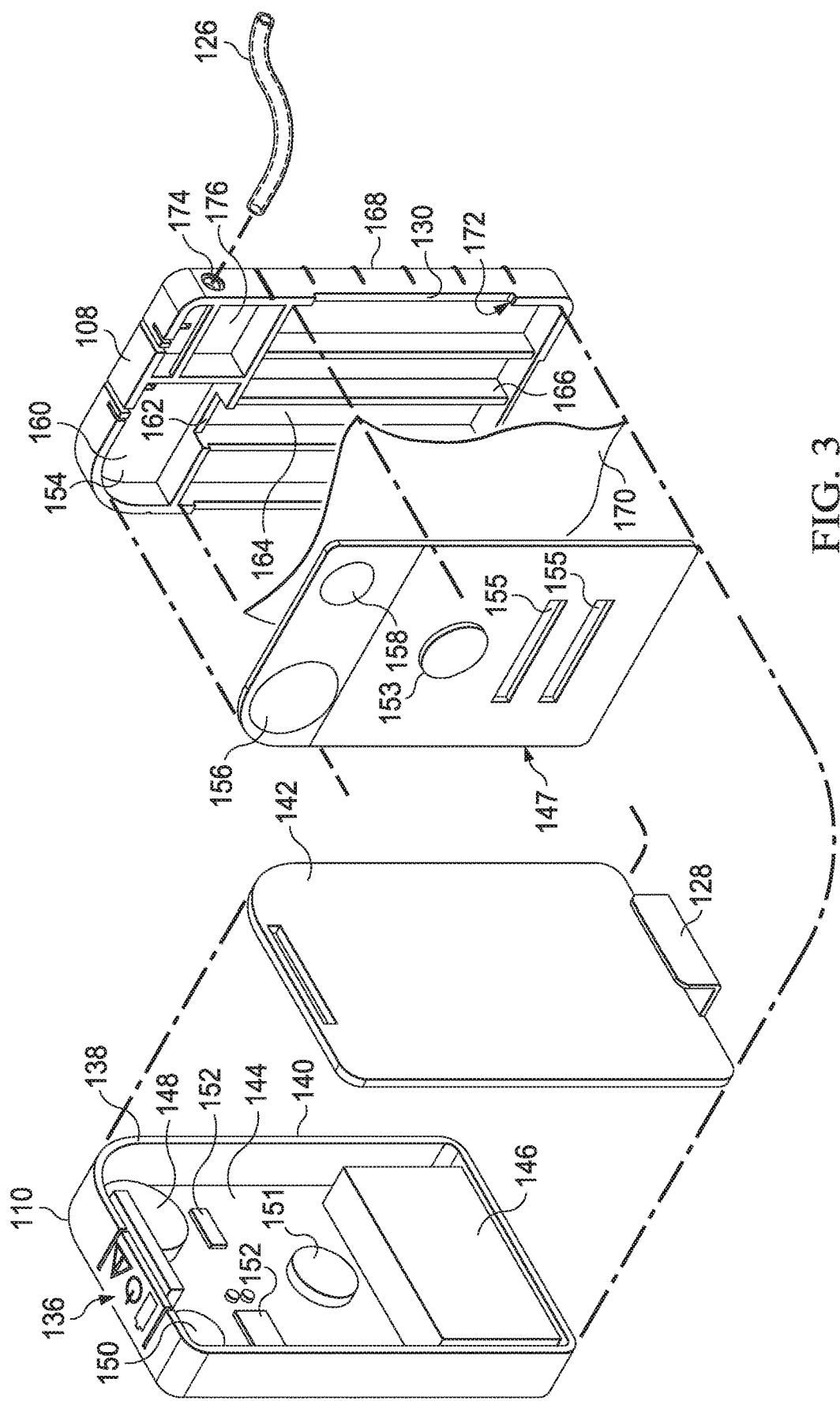
FIG. 3 is a schematic, exploded, perspective view of an illustrative, non-limiting embodiment of a reduced-pressure treatment device.
Figure 4:
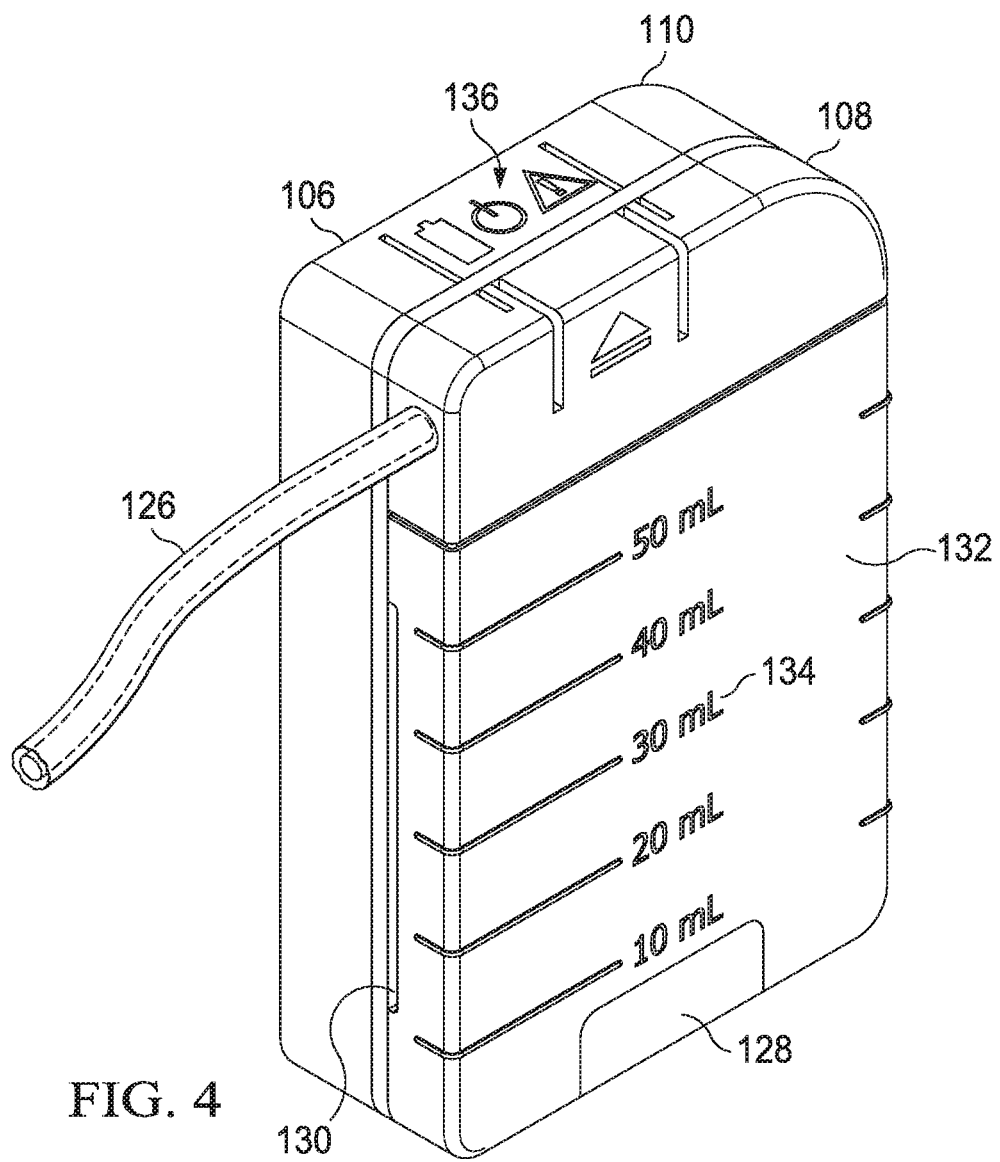
FIG. 4 is a schematic, perspective view of the reduced-pressure treatment device of FIG. 2 shown in an assembled state.

Referring now primarily to FIG. 3, the illustrative reduced-pressure treatment device 106 of FIG. 2 is shown with a few additions or alternatives. An air-movement device 151, e.g., a fan, actuator (that interfaces with a diaphragm as described below), electrostatic device, piezoelectric device, or other device, has been added. The air-movement device 151 may be any device that pushes or pulls air across the membrane 170. In the illustrative embodiment shown, the air-movement device 151 is an actuator in the interior portion 144 of the base portion 140. The actuator, when energized, causes a diaphragm 153 on a second cover 147 to move. The movement of the diaphragm 153 causes air flow across the membrane 170, which in this embodiment is adjacent to the second cover 147 and against baffles 166. The second cover 147 includes vents 155 that allow air to move into an interior portion and against the membrane 170. If a fan is used as the air-movement device 151, the fan may be secured to the first cover 142 and the location shown as diaphragm 153 in FIG. 3 may changed to an aperture sized and configured to align with the fan in order to push air against the membrane 170 and out of the vents 155. Other aspects of FIG. 3 are analogous to FIG. 2.

Referring again primarily to FIG. 2, the reduced-pressure delivery conduit 126 interfaces with a reduced-pressure inlet 174 and delivers fluids to a receiving chamber 176 that is in fluid communication with the pump chamber 160. The second electromagnet 150 may be a second pressure detector that may monitor the level of reduced pressure in the reduced-pressure delivery conduit 126, and consequently, the tissue site 102, by measuring the position of the second diaphragm 158. The position of the second diaphragm 158 is measured via the change in inductance experienced by the second electromagnet 150 as the second diaphragm 158 is displaced. Likewise, the first electromagnet 148 may include a first pressure detector (not shown) that may measure the pressure in the canister unit 108 by measuring the position of the first diaphragm 156 via the change in inductance experienced by the first electromagnet 148 as the first diaphragm 156 moves.

Figure 5:
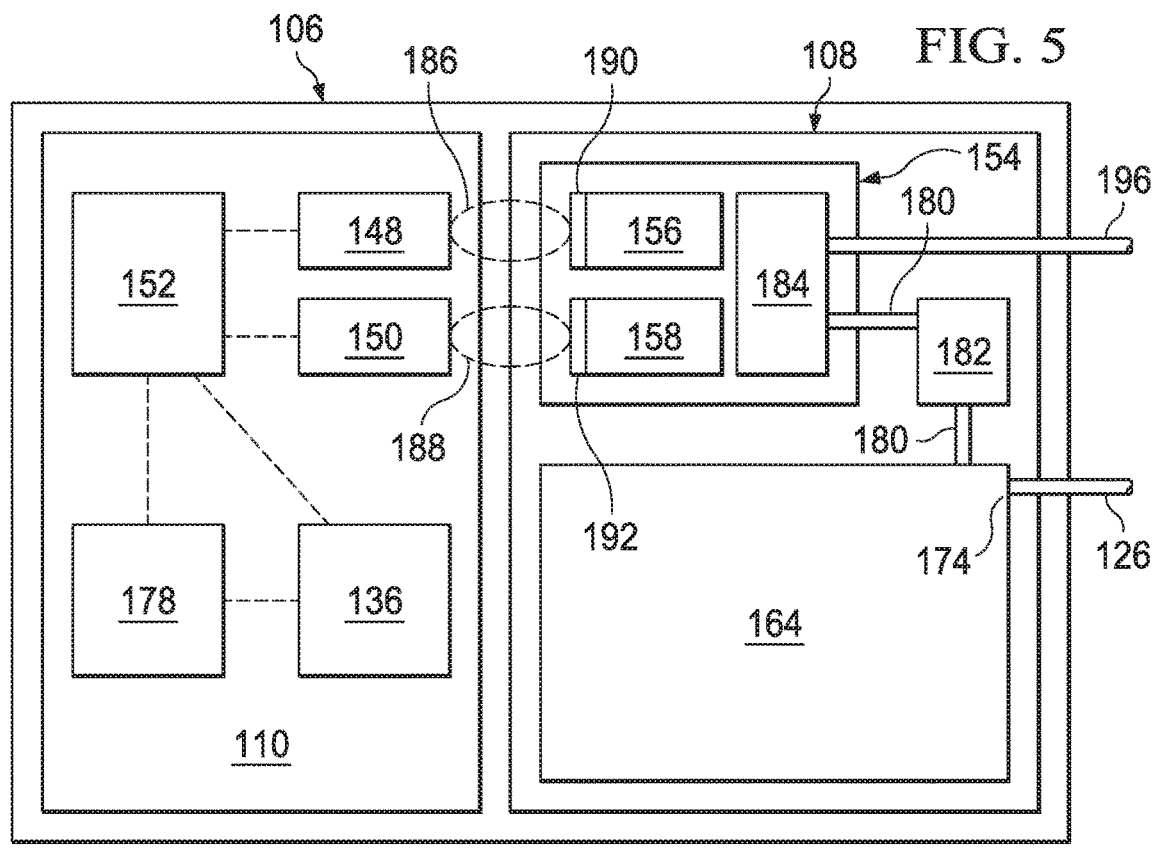
FIG. 5 is a schematic diagram of an illustrative, non-limiting embodiment of a reduced-pressure treatment device.

Referring now primarily to FIG. 5, the reduced-pressure treatment device 106 includes the canister unit 108 and the pump control unit 110. The pump control unit 110 is fluidly separate or isolated from the pump head 154. The pump control unit 110 is also fluidly separate from the canister unit 108. The pump control unit 110 communicates or provides pump energy to the pump head 154. The pump energy in turn moves components, e.g., the first diaphragm 156, on the pump head 154 and that movement is used to generate reduced pressure. In some embodiments, the second diaphragm 158 may be included in the pump head 154 to generate reduced pressure or to measure the reduced pressure.

A valve assembly 184 is associated with the first diaphragm 156 and the pump chamber 160 (FIG. 2). The valve assembly 184 may be, for example, one or more one-way valves (see, e.g., one-way valves 194 in FIG. 6A) that allow fluids to be moved out of the pump chamber 160 to produce a reduced pressure that is communicated to conduit 180. Other techniques for using moving components to produce reduced pressure may be used.

The pump control unit 110 may include the user interface device 136, the control device 152, and a power subsystem 178, such as the batteries 146 (FIG. 2). The pump control unit 110 may be configured for one setting of operation, and in such an illustrative embodiment, power from the power subsystem 178 may be supplied directly to the control device 152. The reduced-pressure treatment device 106 will then produce reduced pressure at the pre-set level.

In another illustrative embodiment, a user may enter parameters into the reduced-pressure treatment device 106, such as a desired pressure range, time duration for operation, or other performance parameters. In this latter illustrative embodiment, the user interface device 136 may be used. The user interface device 136 may be a panel with selector buttons for input as well as a display for presenting information and options to the user. The user interface device 136 may be electrically coupled to the power subsystem 178 and to the control device 152.

The user interface device 136 takes user interaction and translates that into an electrical or software code command for use in the reduced-pressure treatment device 106. The user interface device 136 may be a capacitive or resistive touch panel over (or with) LCD, OLED, or LED screens; membrane panels with buttons and LEDs; enclosure mounted buttons with LEDs; enclosure-mounted capacitive sensors; gesture recognition cameras; or combinations of the aforementioned technologies. In one illustrative, non-limiting embodiment, the user interface device 136 is a basic switch that requires no decoding to determine the command which can be passed onto the control device 152. In another illustrative embodiment, the user interface device 136 is a touch screen and LCD combination that requires a software code to determine the user command. Generally, the user interface device 136 determines and communicates the command from a user to the control device 152, and may send feedback to the user regarding the status of treatment from the control device 152 or module.

The control device 152 controls the treatment administered with the reduced-pressure treatment system 100 and, in this illustrative embodiment, controls the action of the linking interfaces 186, 188 based upon commands from the user via the user interface device 136. The control device 152 translates the power provided by the power subsystem 178 into the pump energy for a first linking interface 186 and a second linking interface 188 as will be described further below and may sequence the linking interfaces 186, 188. In some illustrative embodiments, the control device 152 contains control electronics, such as a microprocessor running therapy code and drive electronics capable of controlling the linking interfaces 186, 188. The power for the control device 152 is derived from the power subsystem 178, which provides power to the reduced-pressure treatment system 100 at the appropriate levels to drive the control device 152 and the linking interfaces 186, 188.

The power subsystem 178 may communicate data and power to the control device 152 and to the user interface device 136. The power subsystem 178 provides the appropriate power for the control device 152 and the user interface device 136 and may provide status information, which can be monitored by the control device 152. The status information may include whether the power subsystem 178 is connected to main power and the status of the battery charge. The status information may be presented to the user via the user interface device 136. The power subsystem 178 also may charge the battery and switch over to the battery if the main power connection is disconnected.

The canister unit 108 includes the fluid reservoir 164 and the pump head 154. In this illustrative embodiment, the reduced-pressure delivery conduit 126 delivers fluids to the fluid reservoir 164 through the reduced-pressure inlet 174. The pump head 154 develops reduced pressure when the pump head 154 receives pump energy. The reduced pressure is delivered through the conduit 180 to the fluid reservoir 164. The conduit 180 may include one or more filters 182, such as a hydrophobic filter, to prevent liquids from contaminating the pump head 154. The canister unit 108 may further include a vent conduit 196 that vents gas from the wound 112 (FIG. 1) to an exterior of the reduced-pressure treatment device 106.

In operation, pump energy is supplied to the pump head 154 by at least one linking interface, such as the first linking interface 186. In this illustrative embodiment, the first linking interface 186 includes the first electromagnet 148 and a first magnetic member 190 associated with the first diaphragm 156. The first magnetic member 190 may be a metal washer, a magnetic part of the diaphragm (or coated on the surface), or other member coupled to the first diaphragm 156.

In some embodiments, the user activates the reduced-pressure treatment device 106 using the user interface device 136. The control device 152 activates the first electromagnet 148 to develop an alternating magnetic field that is magnetically coupled to the first magnetic member 190 on the first diaphragm 156. The first electromagnet 148 may create an electromagnetic field in a direction substantially aligned with the location of the first diaphragm 156. The movement of the first diaphragm 156 in conjunction with the valve assembly 184 allows for the production of reduced pressure that is delivered into the conduit 180 and to the fluid reservoir 164. The reduced pressure then communicates through the reduced-pressure delivery conduit 126 to the tissue site 102. It should be appreciated that the first linking interface 186 allows pump energy to be delivered to the pump head 154 without any fluid communication between the pump control unit 110 and the canister unit 108. Accordingly, contaminants in the canister unit 108—whether gaseous or liquid—cannot reach the pump control unit 110. The more highly-valued components may reside in the pump control unit 110 and are protected from contamination. In one embodiment, the canister unit 108 may be disposable such that fresh canister units may be used with the same pump control unit 110 for ongoing applications.

In some embodiments, the second diaphragm 158 may be used with the second linking interface 188 to generate reduced pressure. The second diaphragm 158 has a second magnetic member 192 and works with the second linking interface 188 in a manner analogous to the first diaphragm 156 and the first linking interface 186. In another embodiment, the second diaphragm 158 may be provided to measure the pressure within the pump head 154.

In this latter embodiment, the displacement of the second diaphragm 158, and particularly the second magnetic member 192, is sensed via the change in induction experienced by the second electromagnet 150. Other techniques may be used for detecting displacement of the second diaphragm 158. For example, the pump control unit 110 may include an infrared sensor that sends an infrared signal onto the second diaphragm 158, and particularly, without limitation, onto the face where the magnetic member 192 is or otherwise would be. The infrared signal returns to the infrared sensor and the distance can be detected and the displacement ascertained.

In another example, the pump control unit 110 may include a capacitance sensor and the second diaphragm 158 may include a plate that when moved changes the capacitance detected by the capacitance sensor on the pump control unit 110. In another embodiment, a ferrite material may be coupled to the second diaphragm 158. A Hall Effect sensor in the pump control unit 110 may be used to sense a change in flux due to movement of the ferrite that allows the displacement to be sensed.

In another embodiment, in addition to or in lieu of measuring displacement of the second diaphragm 158, the pump control unit 110 may have a sensor for determining displacement of the first diaphragm 156 using analogous techniques. In this latter embodiment, the reduced-pressure treatment device 106 may stop providing pump energy to the first diaphragm 156 such that the reduced pressure in the pump head 154 acts on the first diaphragm 156. The sensor may then measure the displacement of the first diaphragm 156. The pressure in the pump head 154 may be determined using the displacement measurement. When both diaphragms 156, 158 are used to measure reduced pressure, one diaphragm may be used to measure the pressure in the pump head 154 and the other diaphragm used to measure pressure at another location such as in a sampling conduit (not shown). The sampling conduit may be associated with the reduced-pressure delivery conduit 126.

Figure 6C:
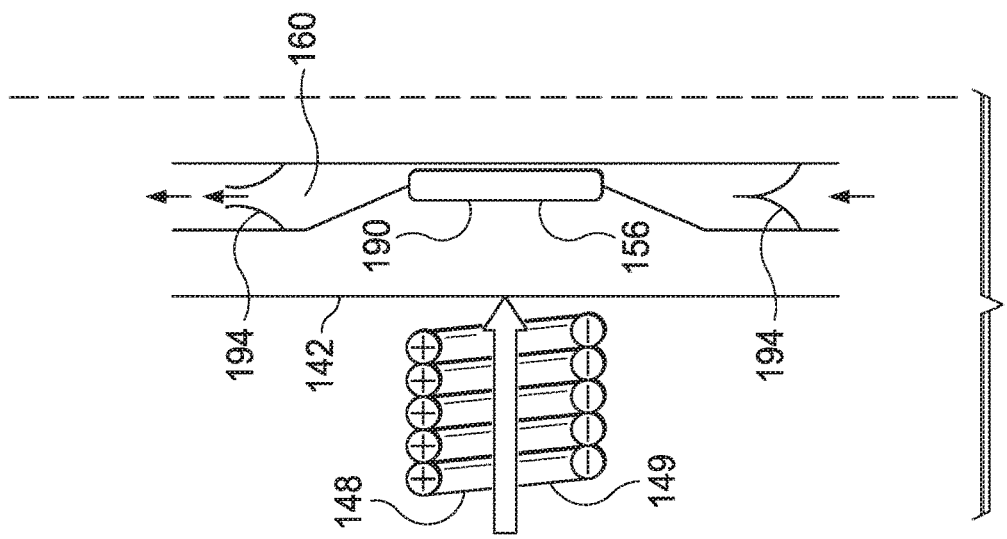
FIGS. 6A-6C are schematic diagrams showing an illustrative, non-limiting embodiment of a linking interface and showing a portion of a pump head in different positions involved with pumping.
Figure 6B:
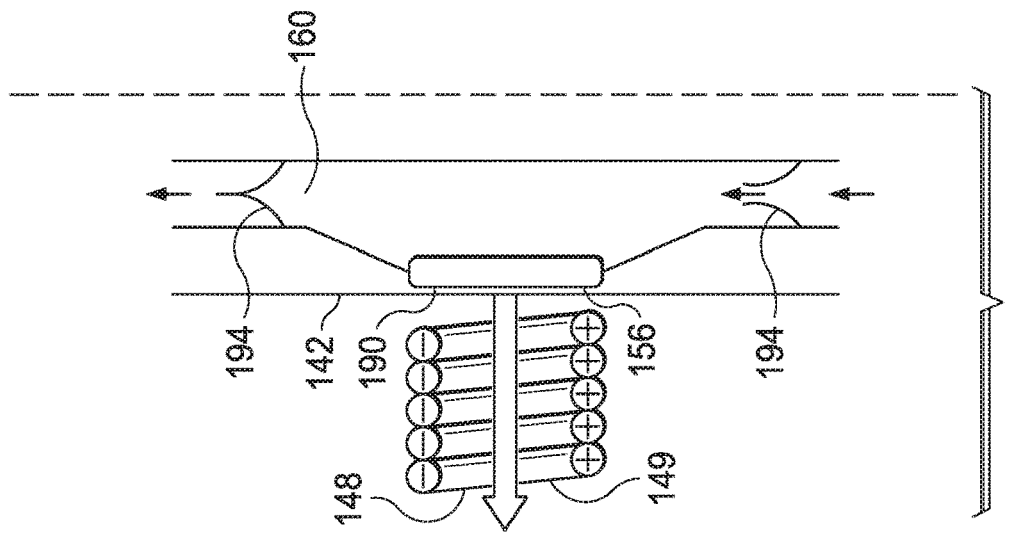
Figure 6A:
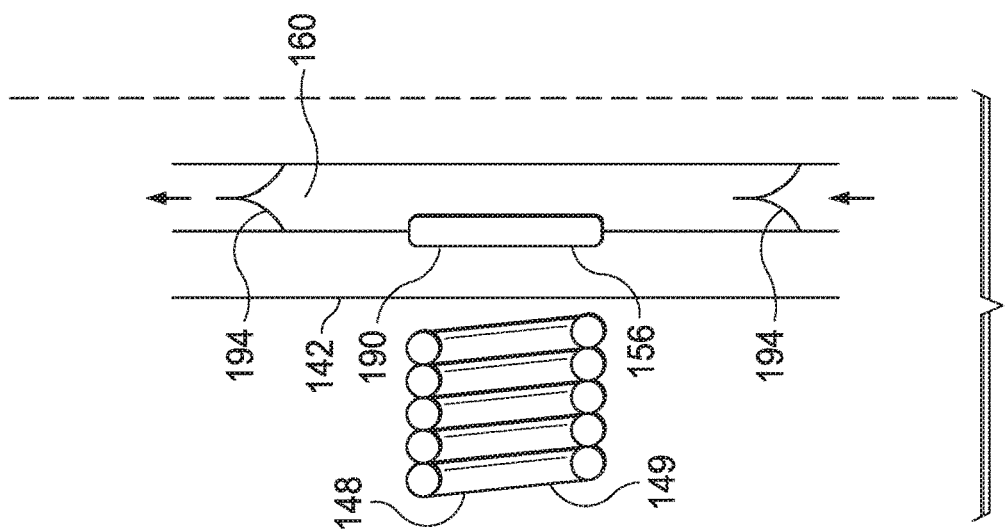

Referring now primarily to FIGS. 6A-6C, a diagram is presented illustrating how the first electromagnet 148, which may be a magnetic coil 149, interacts with the first magnetic member 190 on the first diaphragm 156 and the pump chamber 160 to produce reduced pressure. The first electromagnet 148 may be within the interior 144 (FIG. 2) of the base portion 140 (FIG. 2) and may have the cover 142 disposed between the first electromagnet 148 and the first diaphragm 156. FIG. 6A shows the first electromagnet 148 in the un-energized position, or neutral position. In FIG. 6B, the first electromagnet 148 has been energized and provides an electromagnetic force that acts on the first magnetic member 190. As such, the electromagnetic force urges the first magnetic member 190 towards the first electromagnet 148 to a first position. FIG. 6C shows the electromagnetic force having been reversed such that the first electromagnet 148 urges the first magnetic member 190 away from the first electromagnet 148 to a second position. It should be appreciated that the volume ($V_1$) of the pump chamber 160 in the first position is greater than the volume ($V_2$) in the second position. Thus, fluid in the pump chamber 160 is removed and then, as the first magnetic member 190 is urged back towards the first electromagnet 148, a reduced pressure is created within the pump chamber 160. The reduced pressure remains in the pump chamber 160 because fluid is not pulled back into the pump chamber 160 because of the one-way valves 194.

Referring again primarily to FIG. 1, in operation of the reduced-pressure treatment system 100, the manifold 104 is disposed proximate the tissue site 102. The manifold 104 and a portion of the patient's epidermis 114 are covered with sealing member 120. The sealing member 120 is used to help form a fluid seal over the manifold 104 and the tissue site 102. If not already installed, the reduced-pressure interface 124 is installed to provide fluid access to the manifold 104. The reduced-pressure delivery conduit 126 is used to fluidly couple the reduced-pressure interface 124 to the reduced-pressure treatment device 106.

Then the reduced-pressure treatment device 106 is activated. In some embodiments, the reduced-pressure treatment device 106 may be activated using the user interface device 136. As previously described, activation of the reduced-pressure treatment device 106 energizes the first linking interface 186 and provides pump energy from the pump control unit 110 to the pump head 154. The second linking interface 188 may also provide pump energy from the pump control unit 110 to the pump head 154 and particularly the second diaphragm 158. The pump energy moves at least one diaphragm, e.g., the first diaphragm 156, and develops reduced pressure as previously described. Throughout the operation or at intervals the pressure in the pump head 154 or at the tissue site 102 may be determined by sensing displacement of the diaphragms 156, 158 as previously described.

Figure 7:
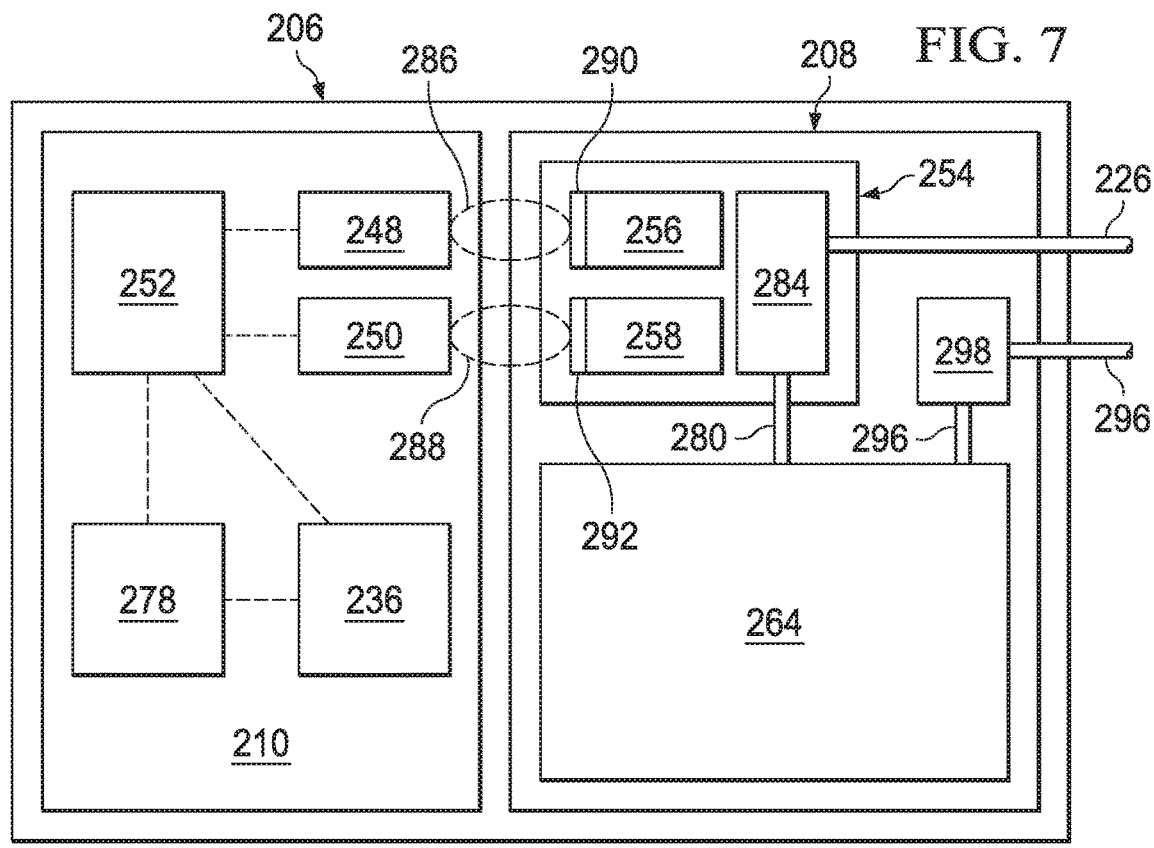
FIG. 7 is a schematic diagram of an illustrative reduced-pressure treatment device showing a pump head acting directly on fluid received from a tissue site.

Referring now primarily to FIG. 7, another illustrative, non-limiting embodiment of a reduced-pressure treatment device 206 is presented. The reduced-pressure treatment device 206 is analogous to the reduced-pressure treatment device 106 of FIG. 5 except that a pump head 254 operates on fluids directly returning from a reduced-pressure delivery conduit 226 that are then delivered by a conduit 280 to a fluid reservoir 264. As in the embodiment of FIG. 5, the reduced-pressure treatment device 206 includes a pump control unit 210 and a canister unit 208. The pump control unit 210 may include controls or a user interface device 236, a power subsystem 278, a control device 252, a first electromagnet 248, and a second electromagnet 250 that are analogous to the user interface device 136, the power subsystem 178, the control device 152, the first electromagnet 148, and the second electromagnet 150, respectively, of FIG. 5.

The canister unit 208 includes the pump head 254. The pump head 254 includes a first diaphragm 256 and a second diaphragm 258 that may have a first magnetic member 290 and a second magnetic member 292, respectively. The pump head 254 may include a valve assembly 284 that operates in conjunction with the first diaphragm 256 to produce reduced pressure. The first diaphragm 256 acts directly on fluids delivered from the reduced-pressure delivery conduit 226. The canister unit 208 may further include a vent conduit 296 that vents gas from the wound, e.g. the wound 112 of FIG. 1, to an exterior of the reduced-pressure treatment device 206. A filter 298 may be added to the vent conduit 296 to prevent liquids and odor from exiting the canister unit 208.

In operation, pump energy is supplied from the first electromagnet 248 to the first diaphragm 256 by a first linking interface 286. The pump energy moves the first diaphragm 256 and creates reduced pressure. The first linking interface 286 includes the first electromagnet 248 and the first magnetic member 290 on the first diaphragm 256. The first linking interface 286 may further monitor pressure in the canister unit 208 by sensing displacement as previously described. Similarly, a second linking interface 288 includes the second electromagnet 250 and the second magnetic member 292 on the second diaphragm 258 for monitoring pressure at the tissue site 102, e.g., the wound 112 of FIG. 1.

Referring still primarily to FIG. 7, but in regard to an alternative illustrative embodiment, the linking interfaces 286, 288 may be a mechanical link. In this illustrative embodiment, the first linking interface 286 may include the first electromagnet 248, a first mechanical actuator (not explicitly shown), and the first diaphragm 256. The first electromagnet 248 receives a first end (proximal end) of a first mechanical actuator (not explicitly shown) and the first diaphragm 256 receives a second, opposing end (distal end) of the first mechanical actuator. When energized, the first electromagnet 248 moves the first mechanical actuator, and the first mechanical actuator in turn moves the first diaphragm 256. The first electromagnet 248 may monitor the pressure in the canister unit 208 by measuring the position of the first diaphragm 256. Similarly, the second linking interface 288 may include the second electromagnet 250, a second mechanical actuator (not explicitly shown), and the second diaphragm 258. The second linking interface 288 may move the second diaphragm 258 to produce reduced pressure. In addition or alternatively, the second electromagnet 250 may monitor the pressure level in the reduced-pressure delivery conduit 226 by measuring the position of the second diaphragm 258 via the second mechanical actuator. The first and second mechanical actuators may optionally include hydraulic fluids. Thus, the first and second linking interfaces 286, 288 operate to move the first and second diaphragms 256, 258, respectively, while remaining fluidly isolated from any of the fluid paths within the canister unit 208.

Figure 8:
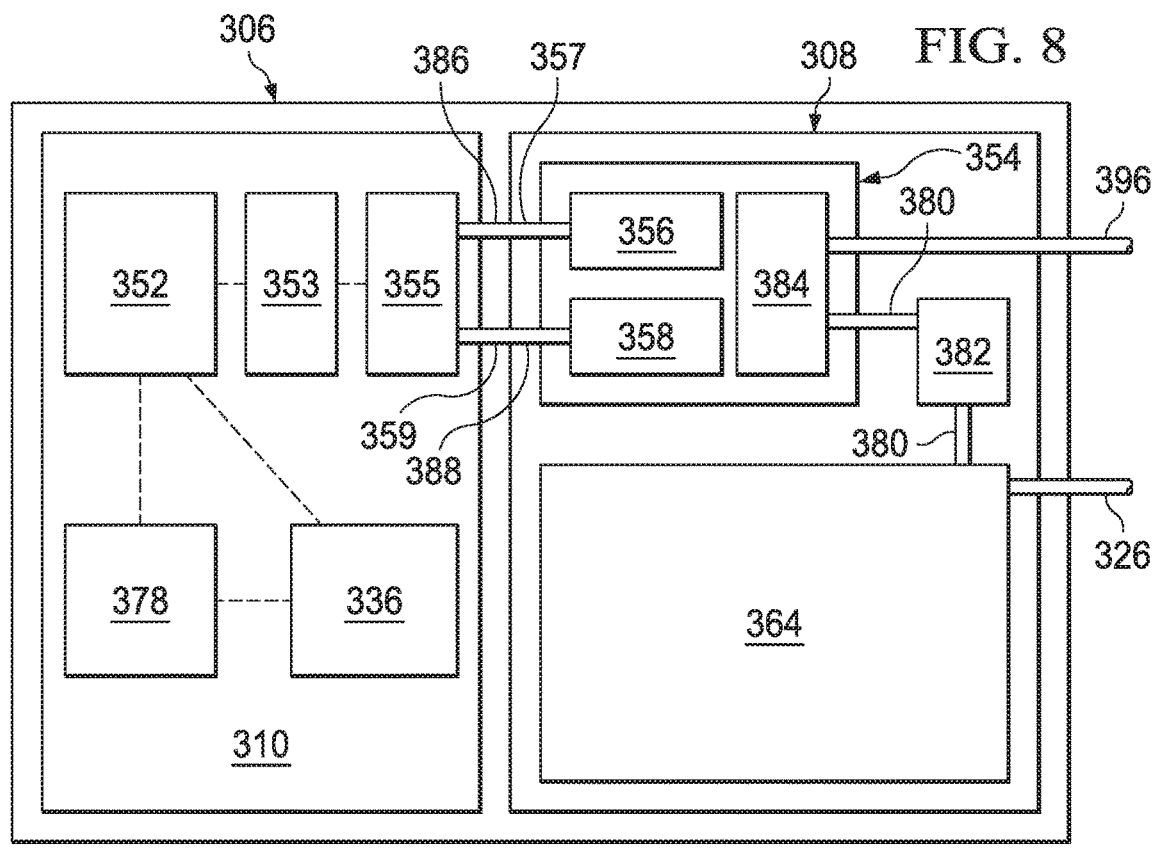
FIG. 8 is a schematic diagram of another illustrative, non-limiting embodiment of a reduced-pressure treatment device.

Referring now primarily to FIG. 8, another illustrative, non-limiting embodiment of a reduced-pressure treatment device 306 is presented. The reduced-pressure treatment device 306 is analogous in most respects to the reduced-pressure treatment device 106 in FIG. 5. For example, the reduced-pressure treatment device 306 includes a canister unit 308 and a pump control unit 310. The pump control unit 310 may include controls or a user interface device 336, which is analogous to the user interface device 136 of FIG. 2. The pump control unit 310 further includes a power subsystem 378. The power subsystem 378 and the user interface device 336 may be electronically coupled to a control device 352. In this illustrative embodiment, the pump control unit 310 further includes a first pump 353 and may further include a valve assembly 355. The first pump 353, alone or in conjunction with the valve assembly 355, provides positive or reduced pressure through a first conduit 357 to a first diaphragm 356 in order to cause the first diaphragm 356 to move. Similarly, a second conduit 359 may provide positive or reduced pressure to a second diaphragm 358.

The canister unit 308 includes a pump head 354, or second pump, that includes the first and second diaphragms 356, 358. A second valve assembly 384 may be included with the pump head 354. The first diaphragm 356, alone or with the second valve assembly 384, operates under the influence of pump energy to produce reduced pressure that is delivered to a conduit 380 and subsequently to a fluid reservoir 364. The conduit 380 may include one or more filters 382, such as a hydrophobic filter. The reduced pressure in the fluid reservoir 364 is delivered to a reduced-pressure delivery conduit 326. The canister unit 308 may further include a vent conduit 396 that vents gas from the tissue site, such as the wound 112 of FIG. 1, to an exterior of the reduced-pressure treatment device 306.

In the reduced-pressure treatment device 306, the first conduit 357 forms a portion of a first linking interface 386. The first linking interface 386 further includes the first pump 353 (and optionally the valve assembly 355) and the first diaphragm 356. The first linking interface 386 may include a first pressure detector (not shown). Thus, positive pressure or reduced pressure generated by the first pump 353 is communicated to the first diaphragm 356 and constitutes pump energy that may be used to develop reduced pressure in the pump head 354. Pressure within the canister unit 308 may be monitored using the first pressure detector (not shown) by measuring the position of the first diaphragm 356. Similarly, the second conduit 359 makes up a portion of a second linking interface 388. The second linking interface 388 also includes the first pump 353 (and optionally the valve assembly 355), the second diaphragm 358, and a second pressure detector (not shown). Pressure at the wound, e.g., the wound 112 of FIG. 1, may be monitored using the second pressure detector (not shown) by measuring the position of the second diaphragm 358.

The first and second linking interfaces 386 and 388, provide a pneumatic coupling between the pump control unit 310 and the canister unit 308. The first pump 353 may be run at a constant load point and may further include a reservoir between the first pump 353 and the valve assembly 355. The first pump 353 can vary the pressure, e.g., go between ambient and a higher pressure, to provide oscillating driving force to the diaphragm 356 or diaphragm 358. In an alternative illustrative embodiment, the first pump 353 may be replaced with a compressed gas vessel and a compressed gas may be provided to the first diaphragm 356 to provide the pump energy to develop reduced pressure in the pump head 354. (It should be noted that the first conduit 357 provides pump energy to the pump head 354, but remains fluidly isolated from the contaminated fluid paths of the canister unit 308.)

Figure 9:
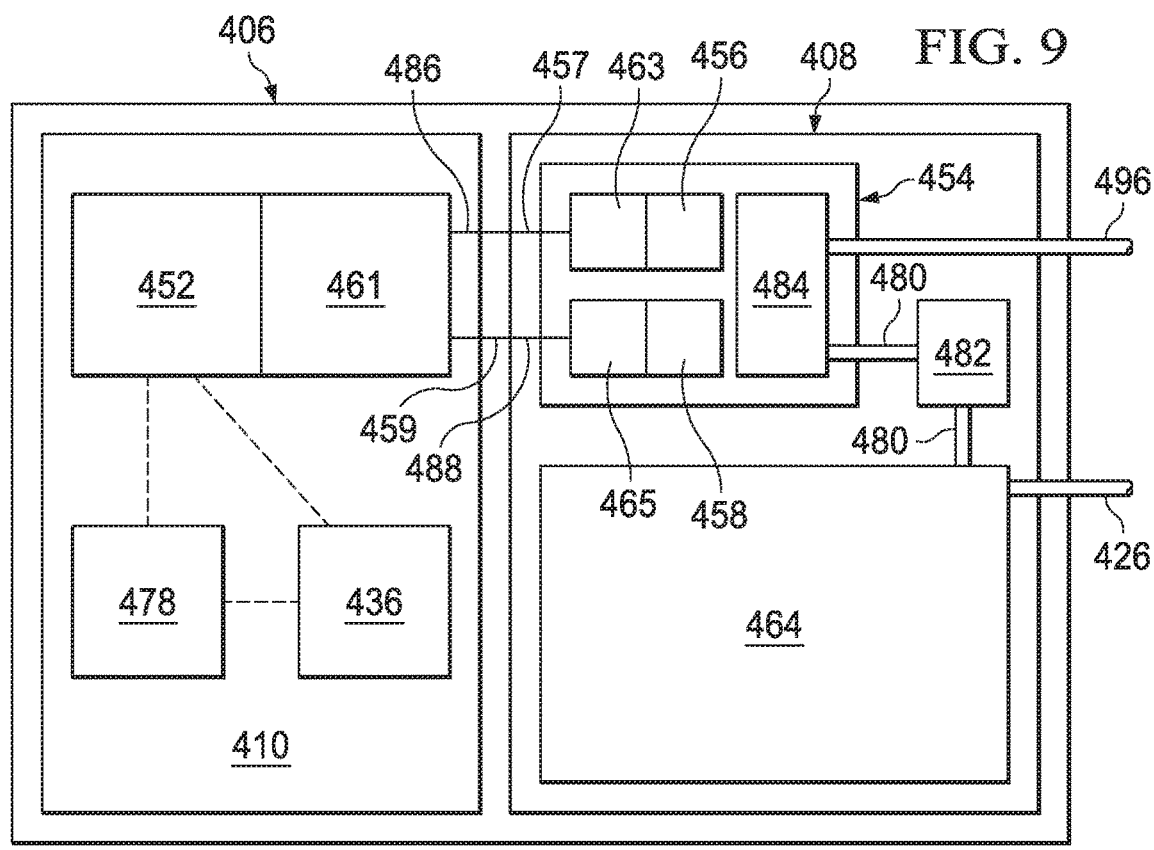
FIG. 9 is a schematic diagram of still another illustrative, non-limiting embodiment of a reduced-pressure treatment device.

Referring now primarily to FIG. 9, another illustrative, non-limiting embodiment of a reduced-pressure treatment device 406 that is analogous in most respects to the reduced-pressure treatment device 106 of FIGS. 1-7 is presented. The reduced-pressure treatment device 406 includes a canister unit 408 and a pump control unit 410. The pump control unit 410 may include controls or a user interface device 436, a power subsystem 478, and a control device 452. As before, the user enters data or desired settings on the user interface device 436. The power subsystem 478 provides power to the control device 452. In this illustrative embodiment, the control device 452 further includes a piezoelectric controller and driver unit 461.

The piezoelectric controller and driver unit 461 is electrically coupled by a first electrical coupling 457 to a first piezoelectric member 463, which is part of or coupled to a first diaphragm 456. Similarly, a second electrical conduit 459 couples the piezoelectric controller and driver unit 461 to a second piezoelectric member 465, which is part of or coupled to second diaphragm 458. Thus, a first linking interface 486 includes the piezoelectric controller and driver unit 461, the first electrical coupling 457, a first pressure detector (not shown), and the first piezoelectric member 463. Pump energy is delivered through the first linking interface 486 to the first diaphragm 456. Pressure within the canister unit 408 may further be monitored by measuring the position of the first diaphragm 456 using the first pressure detector (not shown). Similarly, a second linking interface 488 includes the piezoelectric controller and driver unit 461, the second electrical coupling 459, a second pressure detector (not shown), and the second piezoelectric member 465. Pressure in a reduced-pressure delivery conduit 426 may be monitored by the piezoelectric controller and driver unit 461 by measuring the position of the second diaphragm 458, via the second pressure detector (not shown). The first diaphragm 456 works within a pump head 454 to produce reduced pressure that is delivered by a conduit 480 to a fluid reservoir 464. The conduit 480 may include one or more filters 482, such as a hydrophobic filter. The reduced pressure delivered into the fluid reservoir 464 communicates reduced pressure to the reduced-pressure delivery conduit 426.

In operation, the control device 452 and the piezoelectric controller and driver unit 461 provide a first piezoelectric control signal that is delivered by the first electrical coupling 457 to the first piezoelectric member 463. The first piezoelectric member 463, when energized, causes movement of the first diaphragm 456. The movement of the first diaphragm 456 and the pump head 454 develops reduced pressure that is delivered to the conduit 480. A valve assembly 484 may be included within the pump head 454 to help produce the reduced pressure. The canister unit 408 may further include a vent conduit 496 that vents gas from a wound, such as the wound 112 of FIG. 1, to an exterior of the reduced-pressure treatment device 406.

In another illustrative, non-limiting embodiment (not shown) that is analogous in most respects to the reduced-pressure treatment device 106 of FIGS. 1-5, a reduced-pressure treatment device is presented that includes a pump control unit and a canister unit. The pump control unit may include a user interface device, a power subsystem, and a control device. The user interface device and the power subsystem may be electronically coupled to the control device. The pump control unit may further include one or more laser lights. The canister unit includes a pump head that may have one or more diaphragms that correspond to the one or more laser lights. In operation, pump energy is supplied to the one or more diaphragms by one or more linking interfaces.

In this embodiment, the linking interfaces include the laser light and the diaphragm. The linking interface is operable to deform the diaphragm via laser light to create a pumping action within the pump head to generate reduced pressure. In this illustrative embodiment, the one or more diaphragms may be thermo-reactive diaphragms that may be made from spectra-absorbent polymers that absorb light and which are treated with conductive materials that may help dissipate heat generated by the laser light. The thermo-reactive diaphragms are operable to deform under the application of laser light. In another illustrative embodiment, the one or more diaphragms may be made from a flexible material capable of absorbing a defined wavelength of light to undergo a change in crystalline morphology that changes the density of the material thereby changing the shape of the diaphragm; i.e., the flexible material is operable to deform under the application of laser light.

In view of the foregoing illustrative, non-limiting embodiments of FIGS. 1-9, it should be clear that a "linking interface" is any arrangement for providing energy from the pump control unit to the pump head while keeping the pump control unit fluidly separate or isolated from the potentially contaminated portion of the pump head. In many instances, the linking interface involves using a magnetic field. Other embodiments of the linking interface include using a pneumatic link that moves the diaphragm, using a mechanical actuator that goes between the pump control unit and pump head (on an isolated side of the diaphragm), using laser light as presented in the previous paragraph, and using a piezoelectric member to move the diaphragm.

Systems, devices, and methods for treating a tissue site on a patient with reduced pressure are presented herein. In one instance, a reduced-pressure treatment device to treat a tissue site with reduced pressure may include a pump control unit fluidly separate from a collection unit. Pump energy may be provided by the pump control unit to deflect one or more diaphragms within the collection unit to create reduced pressure. Other systems, devices, and methods are presented.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure treatment device for applying a reduced pressure to a tissue site, the reduced-pressure treatment device comprising:
    a pump head comprising a pump chamber, a diaphragm, and a magnetic member associated with the diaphragm; and
    a pump control unit magnetically coupled to the pump head and comprising an electromagnet configured to:
        provide an electromagnetic force operable to move the diaphragm to a first position; and
        reverse the electromagnetic force to move the diaphragm to a second position.

2. The reduced-pressure treatment device of claim 1, wherein the pump control unit is adapted to measure a displacement of the diaphragm.

3. The reduced-pressure treatment device of claim 1, further comprising one or more one-way valves disposed in the pump chamber.

4. The reduced-pressure treatment device of claim 1, wherein the pump chamber has a first volume when the diaphragm is in the first position and a second volume when the diaphragm is in the second position.

5. The reduced-pressure treatment device of claim 4, wherein the first volume is greater than the second volume.

6. The reduced-pressure treatment device of claim 1, wherein the magnetic member is configured to cycle the diaphragm between the first position and the second position.

7. The reduced-pressure treatment device of claim 1, wherein the electromagnet is fluidly isolated from the diaphragm.

8. The reduced-pressure treatment device of claim 1, further comprising a cover disposed between the diaphragm and the electromagnet.

9. The reduced-pressure treatment device of claim 1, wherein the electromagnet is a magnetic coil.

10. The reduced-pressure treatment device of claim 1, wherein the magnetic member is a metal washer.

11. The reduced-pressure treatment device of claim 1, wherein the pump control unit further comprises a control device and a power subsystem for providing power to the control device.

12. The reduced-pressure treatment device of claim 1, wherein the diaphragm is a first diaphragm and the electromagnet is a first electromagnet, and the pump head further comprises a second diaphragm and the pump control unit further comprises a second electromagnet.

13. The reduced-pressure treatment device of claim 12, wherein the first electromagnet includes a first pressure detector and the second electromagnet includes a second pressure detector.

14. A pump head for applying a reduced pressure to a tissue site, the pump head comprising:
 a pump chamber;
 a first diaphragm forming at least a portion of the pump chamber, the diaphragm configured to receive a pump energy from a pump control unit and further configured to generate a reduced pressure within the pump chamber in response to the pump energy; and
 a second diaphragm fluidly coupled to the pump chamber and configured to measure the reduced pressure.

15. The pump head of claim 14, wherein the pump energy is supplied from the pump control unit to the pump head by at least one linking interface.

16. The pump head of claim 15, wherein the at least one linking interface comprises a magnetic member associated with the diaphragm, the magnetic member configured to be magnetically coupled to an alternating magnetic field developed by an electromagnet associated with the pump control unit.

17. The pump head of claim 14, further comprising a valve assembly.

18. The pump head of claim 17, wherein the valve assembly comprises one or more one-way valves.

19. A pump control unit for applying a reduced pressure to a tissue site, the pump control unit comprising:
 a control device configured to supply a pump energy to at least one linking interface, the linking interface configured to supply the pump energy to a pump head to generate reduced pressure in the pump head;
 a user interface device coupled to the control device and configured to communicate a command from a user to the control device; and
 a power subsystem coupled to the control device and the user interface and configured to power the control device and the user interface device;
 wherein the at least one linking interface comprises an electromagnet associated with the pump control unit and a magnetic member associated with the pump head.

20. Pump control unit of claim 19, wherein the user interface is further configured to communicate feedback from the control device to the user.

* * * * *